(12) United States Patent
DeFreez et al.

(10) Patent No.: US 10,365,199 B2
(45) Date of Patent: Jul. 30, 2019

(54) TWIN-SPOT LIGHT ABSORBING PARTICULATE MONITORING INSTRUMENT

(71) Applicant: Met One Instruments, Inc., Grants Pass, OR (US)

(72) Inventors: Richard K. DeFreez, Azalea, OR (US); Michael A. Potter, Wilderville, OR (US); Thomas L. Pottberg, Grants Pass, OR (US)

(73) Assignee: MET ONE INSTRUMENTS, INC., Grants Pass, OR (US)

( * ) Notice: Subject to any disclaimer, the term of this patent is extended or adjusted under 35 U.S.C. 154(b) by 223 days.

(21) Appl. No.: 15/660,684

(22) Filed: Jul. 26, 2017

(65) Prior Publication Data

US 2019/0033194 A1    Jan. 31, 2019

(51) Int. Cl.
| G01N 15/00 | (2006.01) |
| G01N 15/06 | (2006.01) |
| G01N 15/14 | (2006.01) |
| G01N 21/31 | (2006.01) |

(52) U.S. Cl.
CPC ..... *G01N 15/0625* (2013.01); *G01N 15/1456* (2013.01); *G01N 21/31* (2013.01); *G01N 2015/0046* (2013.01)

(58) Field of Classification Search
CPC ........... G01N 15/0625; G01N 15/0618; G01N 15/1012; G01N 2015/0046
See application file for complete search history.

(56) References Cited

U.S. PATENT DOCUMENTS

| 8,411,272 | B2  | 4/2013  | Hansen |
| 8,531,671 | B1* | 9/2013  | Hansen ............ G01N 15/0625 356/38 |
| 2016/0313229 | A1* | 10/2016 | Drinovec ........... G01N 15/0625 |

OTHER PUBLICATIONS

Smith et al., "Public Health Benefits of Strategies to Reduce Greenhouse-Gas Emissions: Health Implications of Short-Lived Greenhouse Pollutants", The Lancet, 374:2091-2103, 2009.
World Health Organization, "Review of Evidence on Health Aspects of Air Pollution—REVIHAAP Project: Final Technical Report", 2013.

(Continued)

*Primary Examiner* — Blake A Tankersley
(74) *Attorney, Agent, or Firm* — Thomas Schneck

(57) ABSTRACT

An apparatus comprising one or more pairs of analyzers measures light absorbing particulates, including black, brown, and ultraviolet light absorbing organic aerosols, suspended in gaseous samples, such as air. One analyzer receives an ambient gas sample, while the other analyzer is coupled to a dilution inlet that mixes ambient gas with a proportion of clean gas, whereby the two received samples have different particulate concentrations. Filters with identical filter areas accumulate particulates as the respective samples flow through with equal flow rate and velocity. An optical source and detector for each filter measures a changing property (e.g. attenuation at one or more wavelengths) as particulates accumulate. A computer uses the differential particulate accumulation from the ambient and diluted samples to compensate for filter loading effects upon the measurement to provide an accurate indication of particulate concentration in the ambient sample.

19 Claims, 1 Drawing Sheet

(56) References Cited

OTHER PUBLICATIONS

IPCC Fifth Assessment Synthesis Report, "Climate Change 2014", Synthesis Report, 2014.
Andreae et al., "Black Carbon or Brown Carbon? The Nature of Light-Absorbing Carbonaceous Aerosols", Atmos. Chem. Phys., 6:3131-3148, 2006.
Petzoldl et al., "Recommendations for Reporting 'Black Carbon' Measurements", Atmos. Chem. Phys., 13:8365-8379, 2013.
Moosmuller et al., "Aerosol Light Absorption and its Measurement: A Review", Journal of Quantitative Spectroscopy Radiative Transfer, 110:844-878, 2009.
Lack et al., "Characterizing Elemental, Equivalent Black, and Refractory Black Carbon Aerosol Particles: A Review of Techniques, Their Limitations and Uncertainties", Anal. Bioanal. Chem., 406:99-122, 2014.
Bond et al., "Calibration and Intercomparison of Filter-Based Measurements of Visible Light Absorption by Aerosols", Aerosol Science and Technology, 30:582-600, 1999.
Arnott et al., "Towards Aerosol Light-Absorption Measurements with a 7-Wavelength Aethalometer: Evaluation with a Photoacoustic Instrument and 3-Wavelength Nephelometer", Aerosol Science and Technology, 39:17-29, 2005.
Weingartner et al., "Absorption of Light by Soot Particles: Determination of the Absorption Coefficient by means of Aethelometers", J. of Aerosol Science, 34:1445-1463, 2003.
Hitzenberger et al., "Intercomparison of Measurement Methods for Black Carbon Aerosols", Atmospheric Environment, 33:2823-2833, Aug. 1999.
Drinovec et al., "The 'dual-spot' Aethalometer: an improved measurement of aerosol black carbon with real-time loading compensation", Atmospheric Measurement Techniques, 8:1965-1979, 2015.
Virkkula et al., "A Simple Procedure for Correcting Loading Effects of Aethalometer Data", J. Air & Waste Management Assoc., 57:1214-1222, 2007.
Park et al., "Measurement of real time black carbon for investigating spot loading effects of Aethalometer data", Atmospheric Environment, 44:1449-1455, 2010.
Printout: Met One Instruments, BC 1050 and BC 1054 Black Carbon Monitors, 2 pages, published May 2016.
Printout: Met One Instruments, BC-1050 Black Carbon Monitor, 2 pages, published Sep. 2015
Paper: Met One Instruments BC 1050 Monitor, Oct. 4, 2015, 19 pages.

* cited by examiner

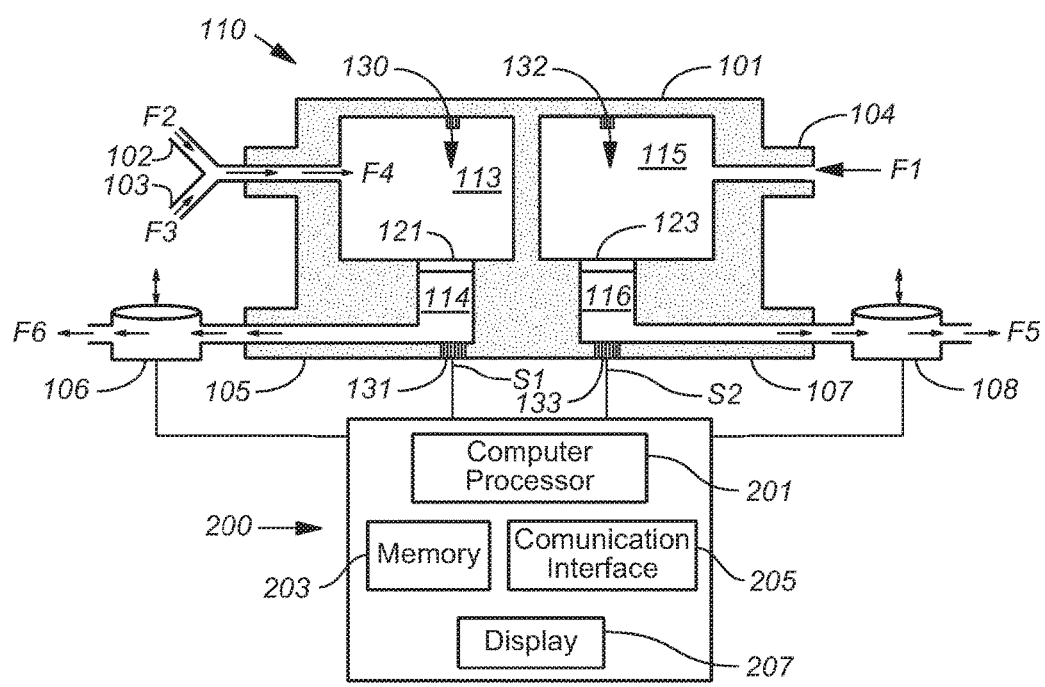

TWIN-SPOT LIGHT ABSORBING PARTICULATE MONITORING INSTRUMENT

TECHNICAL FIELD

The present invention relates to measuring and characterizing aerosols, such as analyzing the concentration of solid particulates suspended in air or another gas, in particular by collecting particles on a support of the filter type and conducting a measurement (e.g. of optical transmittance) upon the filter-deposited material in order to infer the particle aerosol concentration and/or other properties of the aerosol. More particularly, the invention relates to techniques to ensure accuracy in view of filter loading or other non-linear effects upon the measurement.

BACKGROUND ART

Particulate matter (PM) suspended in the atmosphere is a major pollutant affecting both human health and climate forcing. (see for example: Smith, K. R., Jerrett, M., Anderson, H. R., Burnett, R. T., Stone, V., Derwent, R., Atkinson, R. W., Cohen, A., Shonkoff, S. B., Krewski, D., Pope, C. A., Thun, N. J., Thurston, G., "Public Health Benefits of Strategies to Reduce Greenhouse-Gas Emissions: Health Implications of Short-Lived Greenhouse Pollutants", The Lancet, 374:2091-2103, 2009; World Health Organization, "Review of Evidence on Health Aspects of Air Pollution—REVIHAAP Project: Final Technical Report" 2013; IPCC Fifth Assessment Synthesis Report, "Climate Change 2014, Synthesis Report", 2014) There are a wide variety of PM sources and types, including wind-blown mineral dust from agricultural and mining activities, cement dust (calcium silicates and aluminates) from construction activity, fly ash (a coal combustion product containing sulfates and heavy metals), diesel exhaust and other products of incomplete hydrocarbon combustion, as well as other light absorbing organic matter. The latter types include organic carbon (OC), brown carbon (BrC), and black carbon (BC). (Andreae, M. O., and Gelencser, A., "Black Carbon or Brown Carbon? The Nature of Light-Absorbing Carbonaceous Aerosols", Atmos. Chem. Phys., 6:3131-3148, 2006) A unifying terminology for carbonaceous aerosol information derived from optical absorption methods in the ultraviolet, visible, and near infrared wavelength regions is equivalent black carbon (EBC). (Petzoldl, A., Ogren, J. A., Fiebig, M., Laj, P., Li, S.-M., Baltensperger, U., Holzer-Popp, T., Kinne, S., Pappalardo, G., Sugimoto, N., Wehrli, C., Wiedensohler, A., Zhang, X.-Y., "Recommendations for Reporting 'Black Carbon' Measurements", Atmos. Chem. Phys., 13:8365-8379, 2013)

Besides its particular composition, PM can be characterized by particle size or diameter. Inhalable particulates generally have diameters less than 10 μm ($PM_{10}$) These include fine thoracic particulates with diameters less than 2.5 μm ($PM_{2.5}$), which can penetrate into the tracheabronchial and alveolar human respiratory regions and are therefore particularly unhealthy. Ultrafine respirable particulates (or "nanoparticles") have diameters less than 100 nm ($PM_{0.1}$) and can readily enter the circulatory system and then harm other organs.

While all types of particulates are considered to be serious health-threat pollutants, EBC particles that can be very accurately measured optically serve as a stronger indicator of harmful particle substances than does total PM. (World Health Organization, "Review of Evidence on Health Aspects of Air Pollution—REVIHAAP Project: Final Technical Report", 2013; IPCC Fifth Assessment Synthesis Report, "Climate Change 2014, Synthesis Report", 2014). Optical measurements of EBC can be performed with any desired particle size threshold (such as $PM_{2.5}$). Optical determination of EBC has been studied extensively. (See for example: Moosmuller, H., Chakrabarty, R. K., Arnott, W. P., "Aerosol Light Absorption and Its Measurement: A Review" Journal of Quantitative Spectroscopy Radiative Transfer, 110:844-878, 2009; Lack, D. A., Moosmüller, H., McMeeking, G. R., Chakrabarty, R. K., Baumgardner, D., "Characterizing Elemental, Equivalent Black, and Refractory Black Carbon Aerosol Particles: A Review of Techniques, Their Limitations and Uncertainties", Anal. Bioanal. Chem., 406: 99-122, 2014); Bond, T. C., Anderson, T. L., Campbell, D., "Calibration and Intercomparison of Filter-Based Measurements of Visible Light Absorption by Aerosols", Aerosol Science and Technology, 30:582-600, 1999; Arnott, W. P., Hamasha, K., Moosmuller, H., Sheridan P. J., Ogren, J. A., "Towards Aerosol Light-Absorption Measurements with a 7-Wavelength Aethalometer: Evaluation with a Photoacoustic Instrument and 3-Wavelength Nephelometer", Aerosol Science and Technology, 39:17-29, 2005; Weingartner, E., Saathoff, H., Schnaiter, M., Streit, N., Bitnar, B. M., Baltensperger, U., "Absorption of Light by Soot Particles: Determination of the Absorption Coefficient by Means of Aethelometers", J. of Aerosol Science 34:1445-1463, 2003; Hitzenberger, R., Jennings, S. G., Larson, S. M., Dillner, A., Cachier, H., Galambos, Z., Rouc, A., Spain, T. G., "Intercomparison of Measurement Methods for Black Carbon Aerosols", Atmospheric Environment, 33:2823-2833, August 1999, and references cited therein.) In a common method to measure EBC optically, atmospheric aerosols are sampled onto filter media and the attenuation of light through the filter is monitored in real time as EBC-containing particulates accumulate. The change in optical attenuation over time is related to the accumulated quantity of EBC and the flow rate to yield a calculation of EBC concentration. Filter tape may be used in place of discrete filters to extend the period of unattended operation of the EBC monitoring instrument.

In U.S. Pat. No. 8,411,272 to Hansen, and as further explained in a later published paper (L. Drinovec, G. Močnik, P. Zotter, A. S. H. Prévôt, C. Ruckstuhl, E. Coz, M. Rupakheti, J. Sciare, T. Müller, A. Wiedensohler, A. D. A. Hansen, "The 'dual-spot' Aethalometer: an improved measurement of aerosol black carbon with real-time loading compensation", Atmospheric Measurement Techniques, 8:1965-1979, 2015), the measurement accuracy of aerosol black carbon concentration by optical attenuation can be affected by filter tape loading effects, wherein the relationship between attenuation and accumulated EBC becomes nonlinear as attenuation values increase, especially as the filter nears saturation. In order to compensate for this effect, a dual-spot technique is used, wherein the aerosol in the same atmospheric volume is sampled at two different rates either by collecting the EBC sample through different filter areas or by passing the air through the filters at different flow rates, or by switching one or both flows on and off in rapid succession such that the time integrated flow, during the flow collection analytical period, differs between the two collected samples. The non-linear EBC density-attenuation relationship can then be characterized by combining two attenuation measurements. Thus, the compensation parameter can be determined from the actual measurement data instead of being predetermined using a priori assumptions that might not necessarily hold in the particular case, postdetermined (Virkkula, A., Mäkelä, T., Hillamo, R., Yli- Tuomi, T., Hirsikko, A., Hämeri, K., Koponen, I. K., "A Simple Procedure for Correcting Loading Effects of Aethalometer Data", J. Air & Waste Management Assoc., 57:1214-1222, 2007) at each tape advance yielding only a temporally averaged compensation parameter over a collection analytical period, or postdetermined (Park, S. K., Hansen, A. D. A., Cho, S. Y., "Measurement of real time black carbon for investigating spot loading effects of Aethalometer data", Atmospheric Environment, 44:1449-1455, 2010) based on long-term, over many collection analytical periods, statistical analysis yielding an even longer temporally averaged compensation parameter.

However, use of different filter areas or air flow rates can introduce systematic errors of their own. Using either different filter areas with the same flow rate or using different flow rates with the same filter area will produce differences in filter flow face velocities. Different filter flow face velocities can have different impacts upon particles of different sizes and different particle deposition depths in the sample filter, thereby, affecting measurement non-linearities. These can result in uncharacterized contributions to attenuation measurement differences from other than just the accumulation rate, and produce errors in the determined compensation parameter.

It is therefore desired that compensation for filter loading or other non-linear effects upon the measurement be determined without any change to the flow velocity (whether from different filter areas or flow rates) or any other variance that could differentially affect different particle sizes.

SUMMARY DISCLOSURE

An apparatus is provided to measure aerosols of EBC particles (or other optically absorptive aerosol constituents of interest) suspended in two or more gaseous samples, such as air, wherein the samples have different concentrations of the constituents of interest. The apparatus comprises two or more analyzers that receive the different samples with the same flow rate and upon respective filters of equal area. In particular, one of the analyzers is coupled to receive an undiluted ambient gas sample and one or more other analyzers are coupled to a sample dilution inlet configuration so as to receive ambient gas samples that are diluted with one or more specified proportions of clean gas. Each analyzer includes a filter to accumulate constituents of interest in a received sample and a detector to measure a property (e.g. optical attenuation at one or more specified wavelengths) of the constituents of interest accumulating on the filter. Because the flow rates and filter areas are the same for all analyzers, the flow velocity through the filters is also the same, so as not to differentially affect the different sizes of constituent particles or their filter deposition depths. A computer accepts the measurements from each analyzer's detector and from these measurements compensates for filter loading and other nonlinear effects upon the attenuation and provides an accurate indication of the concentration of the EBC particulates (or other constituents of interest) in the undiluted sample.

BRIEF DESCRIPTION OF THE DRAWING

FIG. 1 is a schematic side cross-sectional view of an embodiment of an equivalent black carbon monitoring instrument in accord with the present invention.

DETAILED DESCRIPTION

With reference to FIG. 1, an equivalent black carbon (EBC) monitoring instrument 110 in accord with the present invention may comprise a housing 101 with two analyzer volumes 113 and 115. The two analyzer volumes 113 and 115 are essentially identical, except for certain details regarding their respective inlets 102-104, such that analyzer volume 115 receives an undiluted sample of ambient air F1, while analyzer volume 113 receives a different sample F4 in which clean air F2 has been used to dilute the raw ambient air F3. As such, the two received air samples F1 and F4 will have different concentrations of EBC particles, but otherwise be the same. The clean air F2 could be separately filtered prior to mixing with the ambient air F3, or more preferably may be obtained from the filtered output F5 (or F6) of either analyzer (in order to save filter supplies). The inlets 102 and 103 merge the ambient sample and clean air to form the diluted sample F4 and can be constructed in any fashion that ensures thorough mixing of the clean and ambient air without loss of EBC particulates upon the inlet surfaces. The relative proportions of ambient and clean air F3 and F2 forming the diluted mixture F4 is constant (e.g. 1:1).

Each analyzer volume 113 and 115 is in fluid communication with a filter 121 and 123 to respective analyzer outlet volumes 114 and 116 that are coupled to respective outlets 105 and 107 and pumps (or other flow control devices) 106 and 108. Each filter 121 and 123 has identical filtering areas. Filter tape is preferably used to extend the period of unattended operation of the EBC monitoring instrument. The type of filter tape can be chosen according to the desired particle size threshold to be sampled (e.g. $PM_{10}$, $PM_{2.5}$, $PM_1$, $PM_{0.1}$) and desired filter material (quartz, reinforced glass fiber, fluorocarbon-coated glass, PTFE fibers, etc.). Each filter type requires its own specific calibration, so changing filter types from one to another in any given instrument will necessitate recalibration. When the filter 123 for the raw undiluted sample F1 becomes saturated (as determined by attenuation and/or flow rate measurements), both filters 121 and 123 are advanced to the next clean filter area.

For the pumps 106 and 108, AC or DC gas pumps may be employed. While the flow rates provided by the pumps can be varied according to user specification (e.g. 2 liters per minute (LPM) or 5 LPM), each pump 106 and 108 is controlled so as to provide identical pumping and consequently an identical air flow rate and flow velocity through the respective filters 121 and 123. If desired, a flowmeter can be provided in each output flow path to measure F5 and F6 flow rates and thereby ensure equal pumping.

As EBC particulates are continuously deposited upon the filters 121 and 123, the attenuation of light from respective IR/Vis/UV light sources 130 and 132 passing through the filters is monitored by respective sensors 131 and 133, generating sensor outputs S1 and S2. The light sources may be light emitting diodes. Near infrared light may be 880 nm, 935 nm, 950 nm or some other selected NIR wavelength. These measure absorption by black carbon. Near ultraviolet light may be at 375 nm or some other selected NUV wavelength. This measures absorption by black carbon, brown carbon, and organic carbon. If desired, other wavelengths may be provided, including over visible wavelengths (e.g. 430 nm, 470 nm, 525 nm, 565 nm, 590 nm, 660 nm, 700 nm, and/or other visible wavelengths), for determination of EBC concentration of brown carbon. Measurements can be taken at intervals (1 second, 1 minute, 10 minute, hourly, or some other interval) selected according to desired detection limits, anticipated particulate concentrations, and selected flow rate. This selection enables the instrument to be used over a wide measurement range, i.e. over a minimum of four or five orders of magnitude (e.g. anywhere from <1 ng/m³ to 100 μg/m³). The lower limit of sensitivity might be 8 ng/m³ at 1-minute sampling intervals, but 2 ng/m³ at 30-minute intervals. Increasing the flow rate, say from 2 LPM to 5 LPM, tends to increase the deposition rate for a given particulate concentration, allowing approximately the same sensitivity to be achieved with more frequent measurement intervals.

Because the sample F1 passing through filter 123 is undiluted ambient air, while the sample F4 passing through the filter 121 has been diluted with clean air, the deposition rate of EBC particles will be higher upon the filter 123 even though flow rates and filter areas are identical. This serves as an analytical basis for filter-loading compensation. For example, the technique described in the aforementioned U.S. Pat. No. 8,411,272 to Hansen (and subsequent L. Drinovic et al. paper in *Atmospheric Measurement Techniques* 8:1965-1979, 2015) could be used even though filter collections from two different samples, one ambient and the other diluted, are being sensed in the present case. Now that flow velocities through the two filters 121 and 123 are equal (same filter area and same flow rate), systematic errors arising from differential particle size collection are avoided. The sensor outputs S1 and S2 are supplied to a computer 200, which may comprise a computer processor 201, computer memory 203, communications interface 205, and computer display 207.

As already noted, filter loading has an effect upon the relationship between measured change in attenuation and EBC concentration. The "real" aerosol absorption parameter $b_{abs}$ of airborne EBC is related to the filter-based EBC measurement parameter $b_{ATN}$ by a filter loading coefficient R(ATN), which is dependent upon the amount of filter loading so that $b_{abs}=b_{ATN}/R(ATN)$. The two-spot technique can be used to empirically determine R(ATN) for a given instrument environment, rather than rely upon a priori assumptions.

In order to completely determine the numerical value of R(ATN), the signals S1 and S2 from sensors 131 and 133 can be analyzed in a manner similar to that of the aforementioned Patent and paper, where R(ATN) is given an R(ATN)=1−k*ATN. Attenuation ATN(λ) is defined there as the natural logarithm of the ratio of attenuated light intensity I(λ) and the non-attenuated light intensity $I_0(λ)$ for a clean filter: $ATN(λ)=-\ln[I(λ)/I_0(λ)]$. "k" is the loading compensation factor. Let "y" be the ratio of filter flow concentrations C2 and C1, where for example C2 corresponds to the EBC aerosol concentration of F4 and C1 corresponds to the EBC aerosol concentration of F1. Again as per the aforementioned Patent and paper, the relationship between "y", "k", ATN2 and ATN1 is given by $$y = \frac{\ln(1-k*ATN2)}{\ln(1-k*ATN1)}$$

which must be solved numerically for k.

What is claimed is:

1. An apparatus to measure constituents of interest in gas samples, comprising:
a plurality of analyzers, each analyzer including a filter to accumulate the constituents of interest and an optical source and detector to measure a property of the accumulated constituents of interest on the filter; and
a computer to accept the measurements from each analyzer's detector and to provide an indication of the constituents of interest on each filter,
wherein each of the plurality of analyzers is configured to receive gas samples with different predetermined levels of dilution of an ambient gas sample which have respective concentrations of the constituents of interest corresponding to the level of dilution of the ambient gas sample, each of the plurality of analyzers also receiving the gas samples with the same flow velocity through their respective filters; and
wherein the computer adjusts the indication of the constituents of interest based on the predetermined levels of dilution of the ambient sample gas for each analyzer to account for non-linear filter loading effects.

2. The apparatus as in claim 1, wherein the plurality of analyzers receive the respective different gas samples with the same flow rate and upon respective filters of equal area, such that the flow velocity through the filters is equal in all of the plurality of analyzers.

3. The apparatus as in claim 1, wherein a first analyzer of the plurality of analyzers is configured to receive the ambient gas sample in undiluted form and a second of the plurality of analyzers is coupled to a sample dilution inlet configuration so as to receive the ambient gas sample with a level of dilution determined by a specified proportion of clean gas that is substantially free of the constituents of interest that has been mixed with the ambient gas sample.

4. The apparatus as in claim 1, wherein the constituents of interest include particulates.

5. The apparatus as in claim 4, wherein the particulates comprise one or more of black, brown, or organic carbon.

6. The apparatus as in claim 1, wherein the optical source and detector operate at least at a specified near-infrared wavelength.

7. The apparatus as in claim 6, wherein the optical source and detector also operate at a specified near-ultraviolet wavelength.

8. The apparatus as in claim 7, wherein the optical source and detector also operate at one or more specified visible wavelengths.

9. An apparatus to measure black, brown, and organic carbon particulates in gas samples, said apparatus comprising:
a first analyzer including a first filter having a first filter region to accumulate the black, brown, and organic carbon particulates in a first undiluted ambient air sample having a first flow rate through the first filter, and a first optical source and detector to measure attenuation through the first filter as the black, brown, and organic carbon particulates accumulate thereon;
a second analyzer including a second filter having a second filter region to accumulate the black, brown, and organic carbon particulates in a second diluted air sample which has a concentration of the black, brown, and organic carbon particulates that is a predetermined amount less than the first undiluted ambient air sample, said second diluted air sample having a second flow rate through the second filter that is equal to the first flow rate, the first and second filter regions also being of equal area such that flow velocity through the respective first and second filters are equal, and a second optical source and detector to measure attenuation through the second filter as the black, brown, and organic carbon particulates accumulate thereon; and a computer to accept the first and second detector measurements and determine the concentration of the black, brown, and organic carbon particulates in the respective samples, the computer using the amount of dilution of the second diluted air sample to adjust the determined particulate concentrations for non-linear filter loading effects.

10. The apparatus as in claim 9, wherein the first analyzer is configured to receive the first undiluted ambient air sample and the second analyzer is coupled to a sample dilution inlet configuration that mixes ambient air with a selected proportion of clean gas that is substantially free of particulates to obtain the second diluted air sample.

11. The apparatus as in claim 10, wherein the clean gas is obtained from an outlet of the first analyzer after passing through the first filter.

12. A method for measuring constituents of interest in respective gas samples using one or more pairs of analyzers, for each pair of analyzers the method comprising:

receiving an undiluted ambient gas sample in one of the analyzers and a diluted gas sample in the other of the analyzers, wherein the diluted gas sample is obtained by mixing ambient gas with a specified proportion of clean gas, the samples for each pair of analyzers thereby having different concentrations of the constituents of interest, flowing the respective received samples in each analyzer through a corresponding filter to accumulate the constituents of interest on a filter region of that filter, wherein the filter regions for the pair of analyzers having equal area and the flow rates through the respective filters also being the same such that flow velocity through the respective filters are equal for the pair of analyzers;

measuring at least one specified property of the accumulated constituents of interest on each of the filters; and utilizing the measurements and the specified proportion of clean gas in the diluted gas sample to provide an indication of the constituents of interest in each sample.

13. The method as in claim 12, wherein two or more different pairs of the analyzers have filters and flow rates selected for accumulating constituents of interest of different threshold sizes.

14. The method as in claim 12, wherein the constituents of interest include particulates.

15. The method as in claim 14, wherein the particulates comprise one or more of black, brown, or organic carbon.

16. The method as in claim 12, wherein, for each analyzer, the measuring of the at least one specified property of the accumulated constituents of interest is performed by an optical source and detector operating at least at a specified near-infrared wavelength.

17. The method as in claim 16, wherein the optical source and detector also operate at a specified near-ultraviolet wavelength.

18. The method as in claim 16, wherein the optical source and detector also operate at one or more specified visible wavelengths.

19. The method as in claim 12, wherein the indication is a concentration of black, brown and organic carbon particulates in the respective ambient and diluted samples, and differences in black, brown, and organic carbon accumulation rates upon the respective filters of a pair of the analyzers is used to adjust a determined particulate concentrations for non-linear filter loading effects.

* * * * *